United States Patent [19]
Tornier

[11] Patent Number: 6,165,224
[45] Date of Patent: Dec. 26, 2000

[54] PROSTHESIS INTENDED TO BE ANCHORED IN A LONG BONE

[75] Inventor: Alain Tornier, Saint-Ismier, France

[73] Assignee: Tornier SA, Saint-Ismier, France

[21] Appl. No.: 09/164,769

[22] Filed: Oct. 1, 1998

[30] Foreign Application Priority Data

Oct. 1, 1997 [FR] France .................................. 97 12447

[51] Int. Cl.⁷ .............................. A61F 2/40; A61F 2/38; A61F 2/36
[52] U.S. Cl. ..................... 623/23.21; 623/23.21; 623/606; 623/86
[58] Field of Search .................. 623/23, 23.21, 623/23.26; 606/86, 88, 89

[56] References Cited

U.S. PATENT DOCUMENTS

| | | |
|---|---|---|
| 3,228,393 | 1/1966 | Michele . |
| 4,514,865 | 5/1985 | Harris . |
| 4,623,353 | 11/1986 | Buechel et al. . |
| 4,770,660 | 9/1988 | Averill . |
| 5,047,035 | 9/1991 | Mikhail et al. . |
| 5,100,407 | 3/1992 | Conrad et al. . |
| 5,163,964 | 11/1992 | Lazzeri et al. . |
| 5,258,032 | 11/1993 | Bertin . |
| 5,766,256 | 6/1998 | Oudard et al. . |

FOREIGN PATENT DOCUMENTS

| | | |
|---|---|---|
| 2528307 | 6/1982 | France . |
| 786238 | 1/1997 | France . |
| 821924 | 7/1997 | France . |
| 9716129 | 5/1997 | WIPO . |

Primary Examiner—V. Millin
Assistant Examiner—Choon P. Koh
Attorney, Agent, or Firm—Dowell & Dowell, P.C.

[57] ABSTRACT

A prosthesis for anchoring in a long bone wherein the prosthesis includes a stem adapted to be inserted in a medullary cavity of the bone and from which extends a metaphyseal part which is connected to a flange for bearing on a metaphysis of the bone at a zone of connection. The flange also includes spaced openings for passage of a tool for cutting a reconstituted metaphysis of the bone.

5 Claims, 3 Drawing Sheets

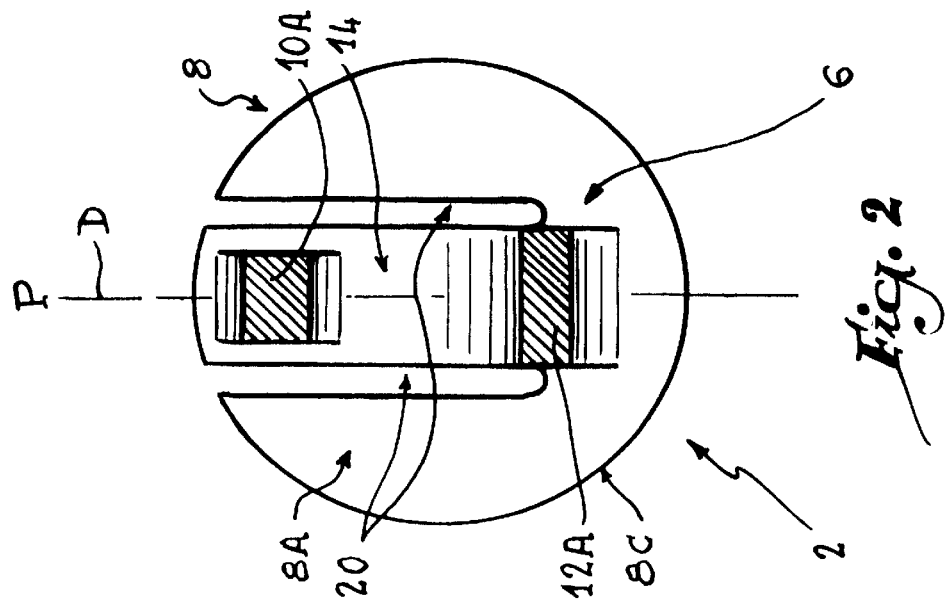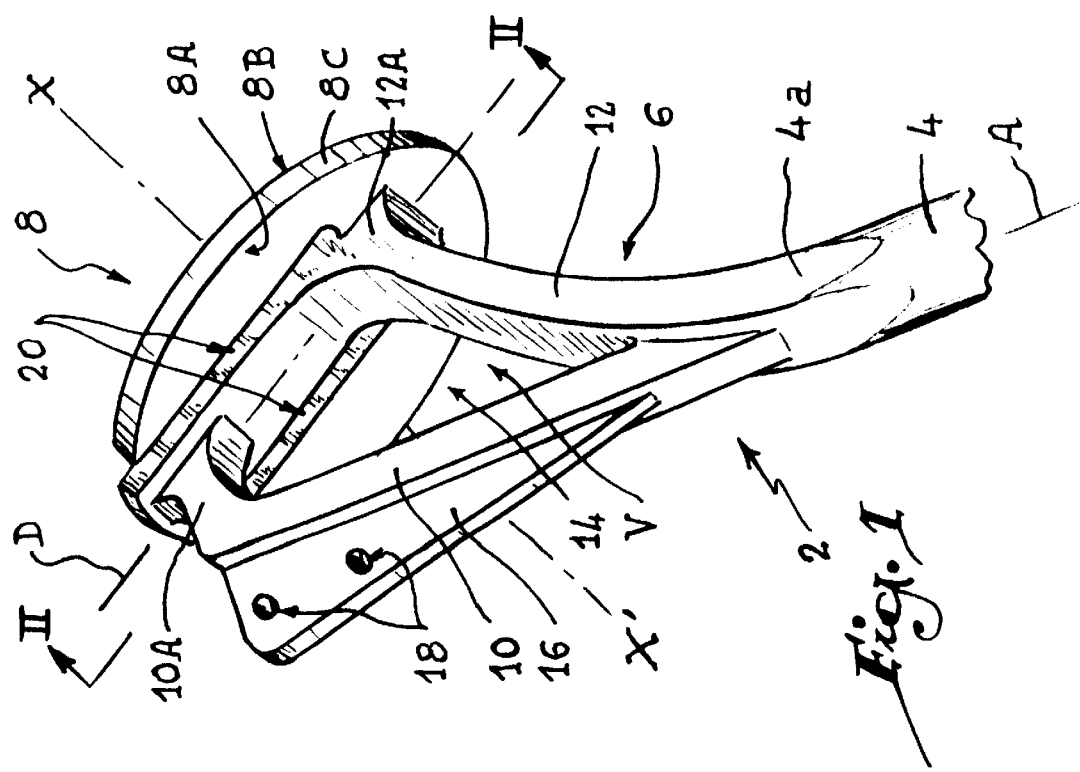

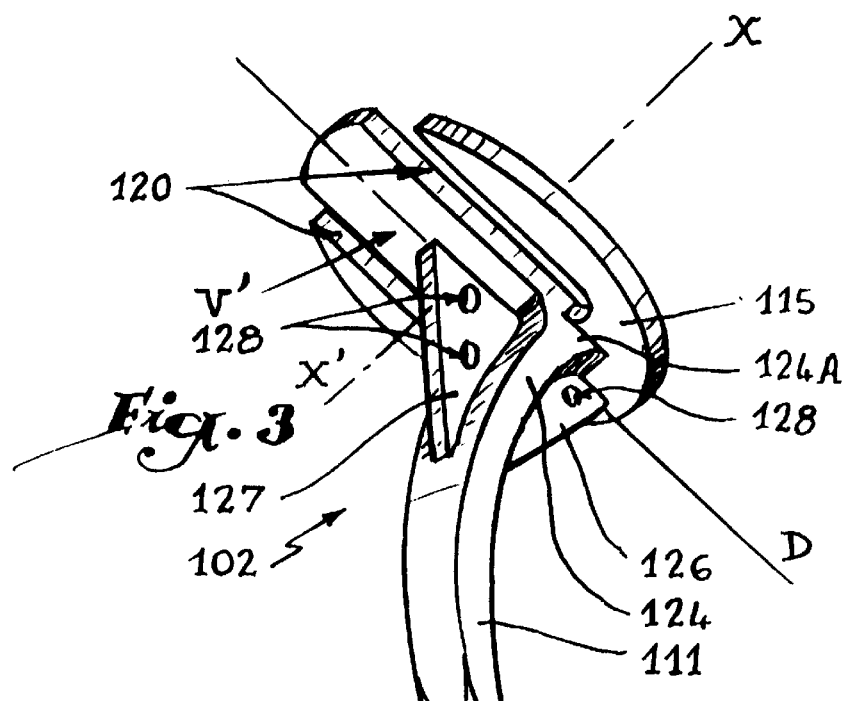
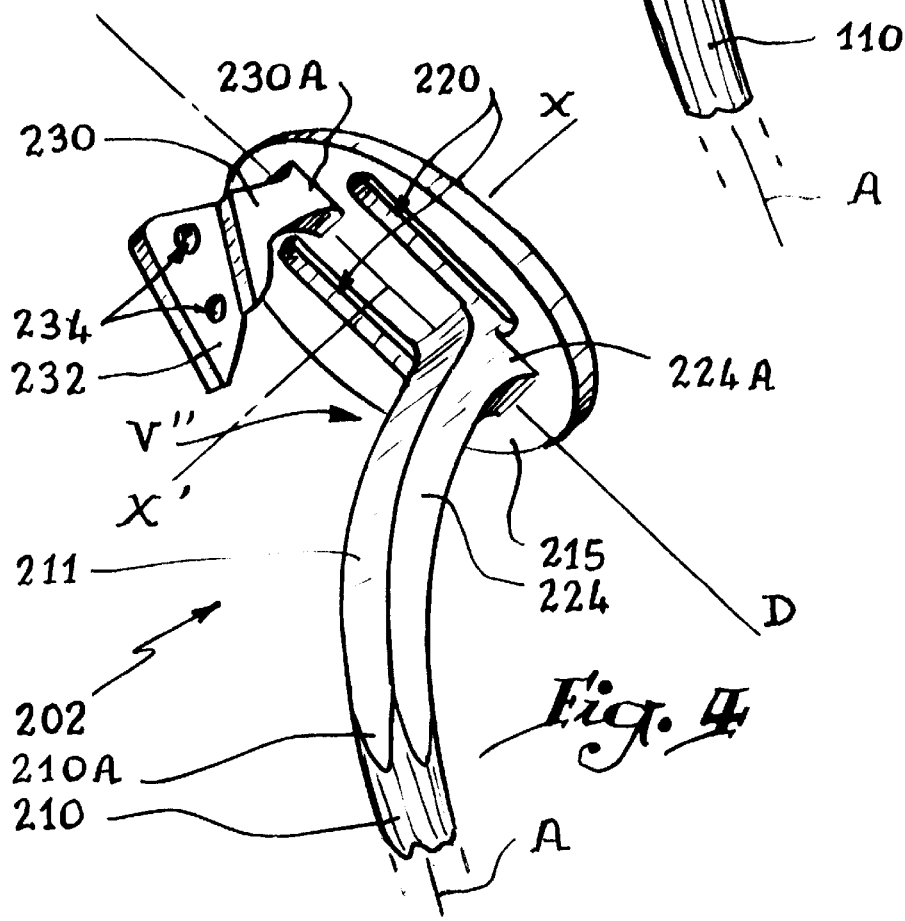

PROSTHESIS INTENDED TO BE ANCHORED IN A LONG BONE

BACKGROUND OF THE INVENTION

1. Field of the Invention

The present invention relates to a prosthesis intended to be anchored in a long bone.

2. History of the Related Art

This type of prosthesis conventionally comprises a stem intended to be inserted in the medullary cavity of the bone, extended by a metaphyseal part connected to a flange allowing bearing on the metaphysis of the bone.

This type of prosthesis can be implanted in particular at the upper end of a humerus, a femur or a tibia, for example in the event of fracture or of disorders such as arthrosis or polyarthritis.

After this prosthesis has been inserted in the bone, the osteosynthesis induces an intimate bonding of the prosthesis and the bone. In effect, the metaphysis of the bone is reconstituted around the corresponding part of the prosthesis and forms protuberances cooperating with reinforcements of the prosthesis, and even an osseous bridge if this latter is provided with a through hole.

However, such intimate bonding and the presence of protuberances or of an osseous bridge may prove to be detrimental, in those cases where it is necessary to remove the prosthesis, particularly in the event of a subsequent operation. In that case, it is necessary to break the reconstituted metaphysis by means of appropriate tools, such as a chisel, bone cutter or drill.

However, this operation proves to be particularly delicate. In effect, the presence of the flange hinders access to the metaphysis of the bone, which lies in the vicinity of that face of the flange opposite the one accessible to the surgeon. He must therefore damage the bone at the lateral surfaces of the flange in order to have access to the metaphysis. Apart from the fact that this operation is delicate for the surgeon, it induces a degradation of the bone over an important surface thereof.

In order to overcome this problem, one known solution consists in providing a prosthesis of which the flange is removable with respect to the stem. Consequently, in the event of subsequent operation or the like, the surgeon removes the removable flange so as to have direct access to the reconstituted metaphysis. However, this solution firstly presents a drawback from the economical standpoint, connected with the mechanical complexity of the prosthesis and the resulting additional costs. Moreover, being given that this prosthesis is inserted in an organic medium, the mechanical elements ensuring the removable clipping of the flange on the stem may be blocked by tissues.

It is therefore an object of the invention to provide a prosthesis which overcomes the drawbacks of the prior art set forth hereinabove.

SUMMARY OF THE INVENTION

To that end, the invention relates to a prosthesis intended to be anchored in a long bone, of the type comprising a stem adapted to be inserted in the medullary cavity of the bone, extended by a metaphyseal part connected, at a zone of connection, to a flange for bearing on the metaphysis of the bone, characterized in that the flange comprises at least one opening for passage of a tool for cutting the reconstituted metaphysis of the bone.

The invention makes it possible to attain the objects mentioned above. In effect, the prosthesis according to the invention presents a simple structure which renders use thereof particularly easy.

Moreover, the presence of the opening enables the surgeon to disconnect the prosthesis from the reconstituted metaphysis of the bone from that face of the flange which is accessible to him, without having to damage the bone at the lateral part of the flange.

The term "tool for cutting the bone" is understood to mean any appropriate tool, such as in particular a chisel, bone-cutter or drill.

According to a first embodiment, the opening for passage of the tool is constituted by at least one oblong slot. This embodiment allows a cutting tool to be used whose attacking face is substantially rectangular, such as for example a chisel or a bone cutter.

This oblong slot may extend radially up to a side of the flange. This enables the surgeon to avail himself of an inclined angle of attack. The terms radial and axial must be understood as being relative to the flange.

According to a second embodiment, the opening for passage of the tool is constituted by a series of orifices, particularly circular ones, of small dimensions. This embodiment allows a cutting tool such as a drill to be used.

According to an additional feature of the invention, the opening for passage of the tool is made in the vicinity of the zone of connection of the metaphyseal part and of the flange, since it is in the vicinity of this zone of connection that it is necessary to separate the prosthesis from the reconstituted metaphysis in order to remove the prosthesis from the bone.

According to another feature of the invention, the metaphyseal part comprises two arms connected to the flange at the zones of connection, and the flange comprises two openings disposed on either side of the axis which joins these zones of connection. In this embodiment, these two arms define therebetween a volume within which the initially splintered osseous fragments of the metaphyseal part are fixed together so as to form an osseous bridge ensuring anchoring of the prosthesis in the bone. The presence of these two openings disposed on either side of the axis of join of the zones of connection of each arm therefore makes it possible to disconnect the osseous volume defined between these arms, with respect to the rest of the bone. The prosthesis may then be easily removed, the osseous bridge possibly remaining in place between these arms.

These two openings advantageously extend at least from the vicinity of the zone of connection between the first arm and the flange, up to the vicinity of the zone of connection of the second arm and the flange.

According to another feature of the invention, the metaphyseal part comprises a single arm extending the stem and connected to the flange at a zone of connection, and the opening extends at least over a substantial part of the perimeter of the zone of connection. In this embodiment, the intimate bonding between the bone and the prosthesis is ensured by the part of the reconstituted osseous metaphysis in the vicinity of the zone of connection. The existence of an opening extending over a substantial part of the perimeter of this zone of connection therefore makes it possible to break this reconstituted metaphysis satisfactorily in order to ensure easy extraction of the prosthesis.

According to a further feature of the invention, the zone of connection is rectangular and the opening extends over the large sides of this zone of connection.

According to another feature of the invention, the metaphyseal part comprises an arm extending the stem and connected to the flange at a zone of connection, as well as a catch projecting from the flange outside the arm, from a zone of connection, and the flange comprises two openings disposed on either side of the axis which joins the zones of connection of the arm and of the catch.

BRIEF DESCRIPTION OF THE DRAWINGS

The invention will be more readily understood on reading the following description with reference to the accompanying drawings, in which:

FIG. 1 is a partial perspective view illustrating a first humeral prosthesis according to the invention.

FIG. 2 is a section along line II—II of FIG. 1.

FIGS. 3 and 4 are partial perspective views illustrating second and third humeral prostheses according to the invention.

DESCRIPTION OF PREFERRED EMBODIMENTS

Figure 5:
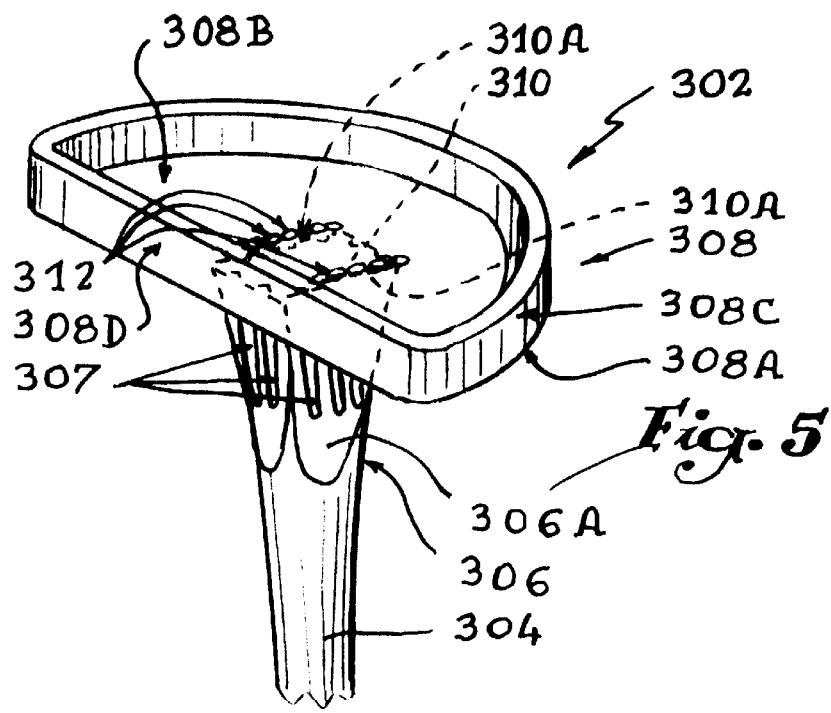
FIG. 5 is a partial perspective view illustrating a tibial prosthesis according to the invention.
Figure 6:
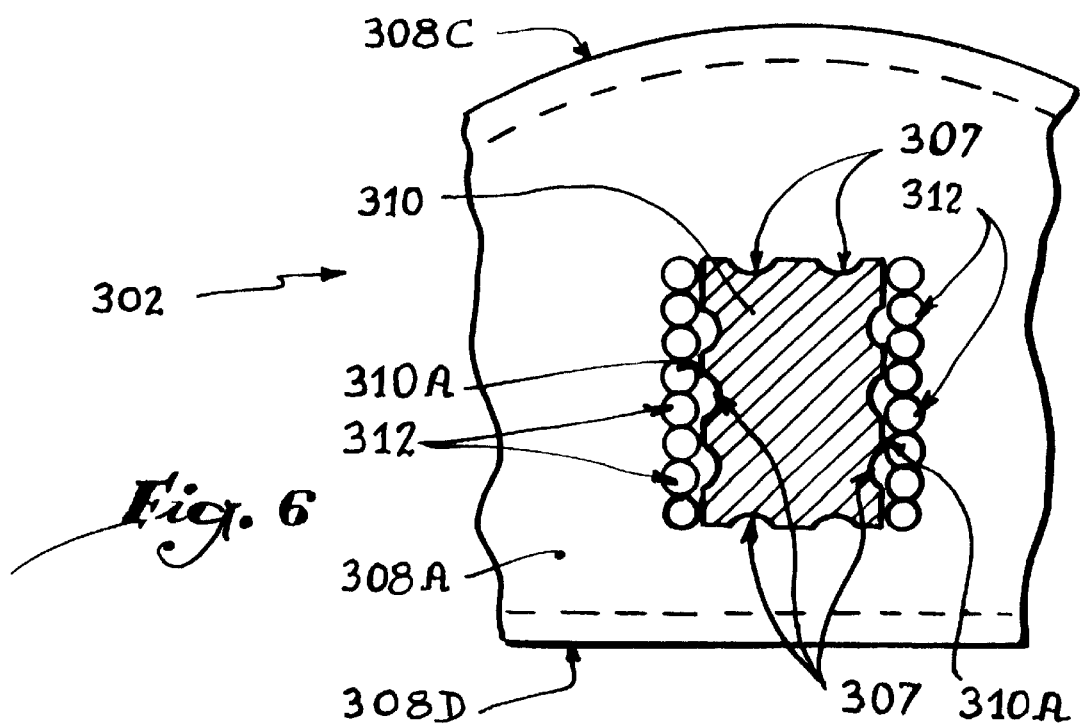
FIG. 6 is a partial section on a larger scale along line VI—VI of FIG. 5.

Before proceeding with the description of the object of the invention, it will be useful to define a certain number of terms: "lower", "upper", "inner" and "outer" must be understood as referring to prostheses carried by a patient standing up.

Referring now to the drawings, the prosthesis shown in FIG. 1 and generally designated by reference 2, is a humeral prosthesis intended to support a hemispherical dome (not shown) adapted to cooperate with the glenoidal cavity of a patient's shoulder.

This prosthesis comprises a stem 4 of substantially circular cross-section which engages in the humeral canal, extended by a metaphyseal part 6 to which is connected a flange 8 intended to abut on a metaphysis of the humerus.

This metaphyseal part 6 comprises an outer arm 10 and an inner arm 12 which are each connected to the lower face 8A of the flange 8 by respective zones of connection 10A, 12A. These latter lie substantially along a median axis of the flange, namely the diameter D of the flange disposed in the same plane P as the axis A of the stem 4 of the prosthesis.

The zones of connection 10A, 12A extend only over a fraction of this median axis so as to define, outside the zone of connection 12A of the inner arm 12, a recess 14 constituting a free volume V for joint and fusion of the fragments of bone of the metaphysis. The existence of this free volume allows the formation of an osseous bridge ensuring anchoring of this prosthesis in the humerus.

The outer arm 10 has a cross-section smaller than that of the arm 12 and extends outwardly by a fin 16 whose transverse dimension is less than that of the arm 10. This fin comprises perforations 18 allowing the passage of suture threads.

The flange 8 is fitted, by its inclined upper face 8B in a corresponding recess in the dome (not shown) intended to replace the humeral head. According to the invention, the flange 8 is provided with two oblong through slots 20, disposed substantially symmetrically on either side of the diameter D. Each slot 20 extends radially from the zone of connection 12A of the inner arm 12, in the direction of the vicinity of the zone of connection 10A of the outer arm 10, and up to the lateral walls 8C of the flange adjacent the outer arm 10. The width of these slots 20 is such that it allows the passage of a bone-cutting tool.

Should it prove necessary to remove the prosthesis 2 from the bone in which it is implanted, the surgeon may, thanks to the presence of the slots 20, cut the osseous bridge formed within the recess 14, from the upper face 8B of the flange 8 which is accessible to him. Since the slots extend up to the lateral walls 8C of the flange, the surgeon avails himself of an angle of attack which may be directed either parallel to axis XX' of the flange, or perpendicular to this axis, or which may be inclined with respect to this axis.

Moreover, being given that these slots 20 are arranged on either side of the diameter D of the flange, the surgeon is in a position to break the osseous bridge in two places, so as to be able to disconnect the osseous zone housed in the recess 14, with respect to the rest of the humerus. It will then be easy for him to remove the prosthesis.

FIG. 3 shows a second embodiment of the prosthesis according to the invention.

Prosthesis 102 differs from the prosthesis 2 shown in FIG. 1 in that its metaphyseal part 111 is no longer constituted by two arms, but by a single arm 124 of which the concavity is directed inwardly. This single arm 124 extends the stem 110 so as to join the flange 115 at a zone of connection 124A disposed substantially on the diameter (D) of the flange, coplanar with respect to axis (A) of the stem 110 of the prosthesis. This zone of connection 124A extends only over a fraction of this diameter so as to define, outside the arm 124, a free volume (V') for joint and fusion of the fragments of bone of the metaphysis. Two fins, inner (126) and outer (127) respectively, provided with perforations 128, project from that face of the flange opposite the face for receiving the dome and extend up to arm 124.

The flange 115 is provided with slots 120 similar to those 20 shown in FIG. 1. The slots enable the surgeon to break the reconstituted metaphysis in the vicinity of the zone of connection 124A of the arm. This flange 115 may likewise be provided with a series of orifices of small dimensions, extending over a substantial fraction of the zone of connection 124A.

FIG. 4 shows a third embodiment of the prosthesis according to the invention.

The prosthesis 202 shown in FIG. 4 differs from the one shown in FIG. 3 in that the arm 224 is not provided with fins. The metaphyseal part 211 of the prosthesis 201 is completed by a catch 230 projecting from the outer portion of the flange, in the direction opposite a dome (not shown).

The arm 224 and the catch 230 are each connected to the flange 215 by respective zones of connection 224A and 230A. These latter are disposed substantially on the diameter (D) of the flange, coplanar with respect to the axis (A) of the stem 210 of the prosthesis. These zones of connection extend only over a fraction of this diameter so as to define, between the arm 224 and the catch 230, a free volume (V") for joint and fusion of the fragments of bone of the metaphysis.

The catch 230 is extended by a fin 232 flared in the direction of the stem 210. This fin 232 has transverse dimensions smaller than those of the catch 230, and is provided with perforations 234 allowing passage of suture threads.

Being given that the catch does not extend as far as the proximal part 210A of the stem 210, the free volume (V") of joint and fusion of the fragments of bone is open at the level of this part 210A. Moreover, the presence of the catch 230 ensures a bearing for the spongy bone and prevents it from collapsing.

The flange 215 is provided with slots 220 which differ from those 20 and 120 shown in the preceding Figures. In effect, they do not open out at the lateral walls of the flange, but extend solely from the vicinity of the zone of connection 224A of the arm 224 up to the vicinity of the zone of connection 230A of the catch 230. The slots 220 make it possible to separate from the prosthesis the metaphysis of the bone, reconstituted in the vicinity of the zones of connection 224A and 230A, by inserting a chisel parallel to the axis XX' of the flange 215.

The prosthesis shown in FIG. 5 and generally designated by reference 302, is a tibial prosthesis which comprises, in known manner, a stem or pin 304 of substantially circular cross-section, extended by a metaphyseal part 306 which comprises a single arm 306A of rectangular cross-section and is connected to the lower face 308A of a flange 308 forming a tibial plate.

This tibial plate is conventionally shaped substantially as a half disc and comprises an edge 308C of curved profile, and an edge 308D of rectilinear profile. These edges 308C, 308D comprise means (not shown) allowing the removable bonding of a tibial plate known per se, likewise not shown.

The metaphyseal part 306 is connected to the lower face 308A of the tibial plate 308 by a substantially rectangular zone of connection 310.

This metaphyseal part 306 is provided, on its outer periphery, with flutings 307 which allow the formation of osseous protuberances ensuring a satisfactory anchoring of the prosthesis in the bone.

Two series of substantially circular through orifices 312 are made in the flange 308, on either side of the large sides 310A of the zone of connection 310. The transverse dimensions of these orifices 312 are such that they ensure the passage, from the upper face 308B of the tibial plate 308, of drills for cutting the bone.

Should the prosthesis 302 have to be withdrawn from the bone after implantation, particularly in the event of a subsequent operation, the surgeon is in a position to cut the metaphysis reconstituted around the pin 304, present in the vicinity of the zone of connection 310. In fact, the surgeon can reach this metaphysis from the upper face 308B of the tibial plate 308 which is accessible to him, by means of drills engaged in the through orifices 312.

In addition, these orifices 312 are disposed over a major part of the perimeter of the zone of connection, which allows the surgeon to break a substantial part of the osseous protuberances so as to render extraction of the prosthesis easier.

In a variant, other orifices, similar to those 312 shown, may also be provided on the small sides of the rectangular zone of connection 310, without, however, rendering the prosthesis mechanically fragile. In place of these orifices 312, one or more oblong slots extending over the major part of the perimeter of the zone of connection may also be provided. The zone of connection may also present a cross-section of different shape, such as for example circular, polygonal or even in the form of a cross.

The present description has been made solely with reference to tibia and humerus prostheses. The invention is also applicable to other long bones, such as in particular the femur, or another other hollow site in which the presence of a flange hinders access to the anchoring stem of the prosthesis when ablation thereof is necessary.

What is claimed is:

1. A prosthesis to be anchored in a long bone comprising; a stem adapted to be inserted in a medullary cavity of a bone and extended by a metaphyseal part connected, at a zone of connection, to a flange for bearing on a metaphysis of the bone, said metaphyseal part including two spaced arms connected to said flange at said zone of connection, wherein said flange includes two openings disposed on either side of said zone of connection for passage of a tool for cutting reconstituted metaphysis of the bone.

2. The prosthesis of claim 1, wherein said openings are constituted by oblong slots.

3. The prosthesis of claim 2, wherein said oblong slots extend radially to a side of said flange.

4. The prosthesis of claim 1, wherein said openings are constituted by a series of orifices which are generally circular.

5. The prosthesis of claim 1 wherein said two openings extend from a first portion of said zone of connection between a first of said two arms and said flange to a second portion of said zone of connection between a second of said two arms and said flange.

* * * * *